United States Patent [19]

Kirkley

[11] Patent Number: 5,152,766
[45] Date of Patent: Oct. 6, 1992

[54] FEMORAL WIRE GUIDE INSTRUMENT

[76] Inventor: William H. Kirkley, Box 332A, Route 2, Columbia, S.C. 29212

[21] Appl. No.: 640,890

[22] Filed: Jan. 14, 1991

[51] Int. Cl.⁵ .............................................. A61B 17/00
[52] U.S. Cl. ..................................... 606/103; 606/86; 606/96
[58] Field of Search ....................... 606/53, 86, 96, 97, 606/98, 103, 104; 24/115 R, 115 L

[56] References Cited

U.S. PATENT DOCUMENTS

| 4,347,845 | 9/1982 | Mayfield | 606/86 |
| 4,360,012 | 11/1982 | McHarrie et al. | 606/96 X |
| 4,383,527 | 5/1983 | Asnis et al. | 606/96 |
| 4,788,970 | 12/1988 | Kara et al. | 606/96 |
| 4,917,111 | 4/1990 | Pennig et al. | 606/97 |

Primary Examiner—Robert A. Hafer
Assistant Examiner—Sam Rimell
Attorney, Agent, or Firm—Hopkins & Thomas

[57] ABSTRACT

An instrument for holding and guiding a wire that is being drilled through the piriformis sinus in the trochanteric region is disclosed, the drilled canal thus formed serving as an entryway into the intermedullary canal of the femur for stabilizing femoral fractures. The instrument includes spaced post members with grooves formed therein to provide a straight path into the sinus and to stabilize the flexible drilling wire for avoiding eccentric movement of the wire during drilling.

19 Claims, 3 Drawing Sheets

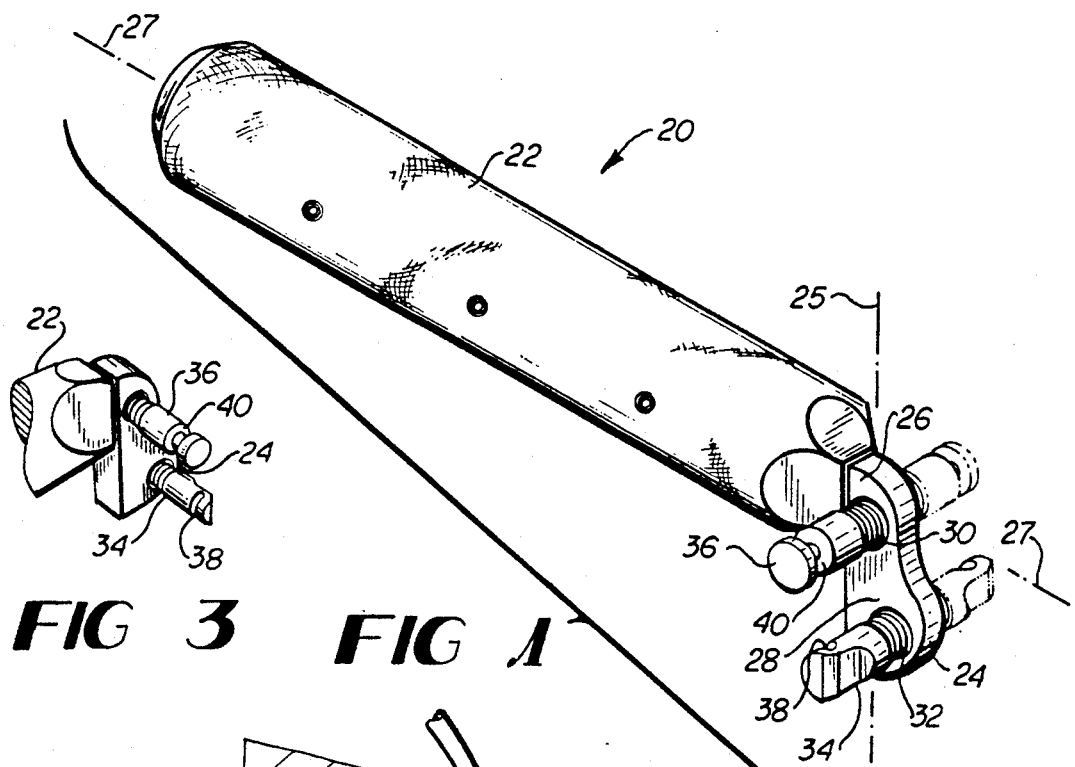
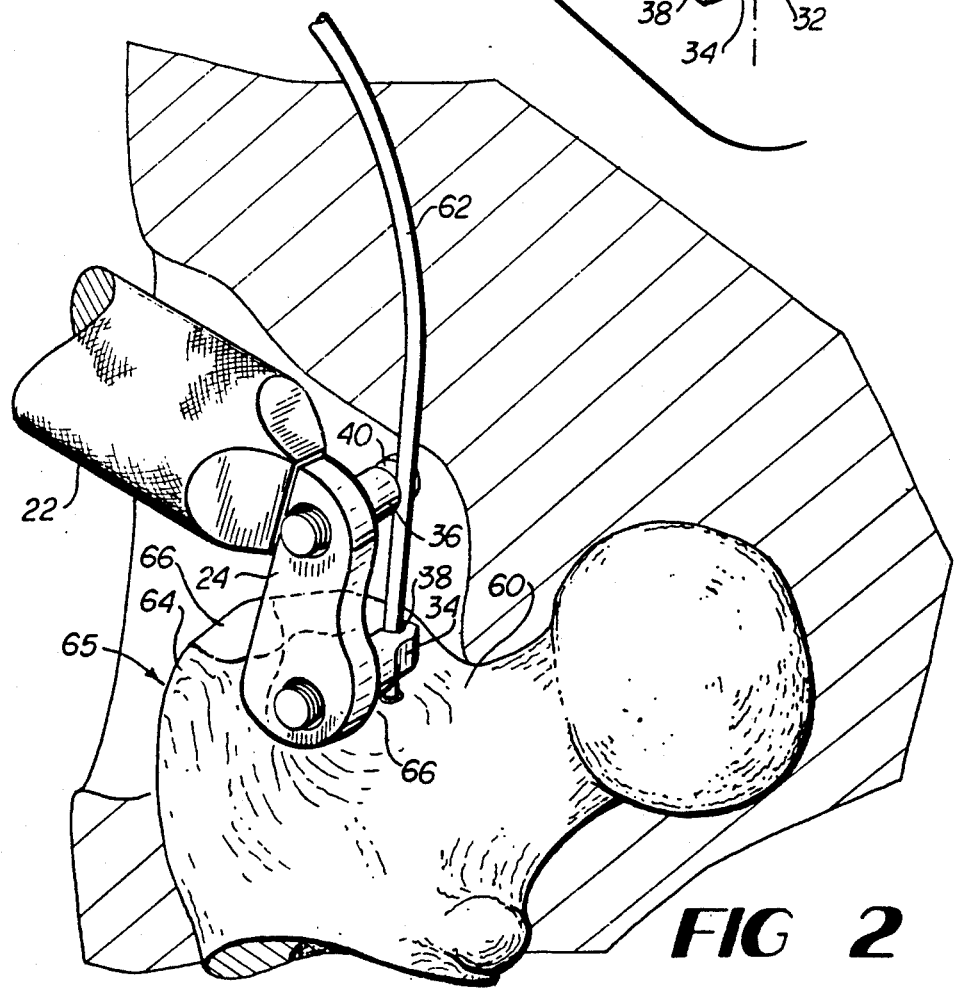

5,152,766

FEMORAL WIRE GUIDE INSTRUMENT

FIELD OF THE INVENTION

This invention relates to the field of orthopedic surgery and more particularly to the stabilization of long bone fractures as in a fracture of the femur. Of the various techniques used for treating femoral fractures, the technique known as closed intramedullary nailing is a type of internal fixation of the bone which minimizes the risks of infection and nonunion and which also allows the patient to become ambulatory shortly after the surgery.

BACKGROUND OF THE INVENTION

In the case of a fracture of the femur, particularly in adults, it is relatively common to utilize internal fixation of the bone to stabilize the fracture site or sites and to facilitate healing. One such technique is closed intramedullary nailing in which an elongated implant, such as a rod, nail, pin, or the like is inserted longitudinally through the intramedullary canal of the bone. The procedure normally involves making a small incision in the buttocks and entering the canal of the femur through the lower portion of the greater trochanter. A guide pin is inserted and a cannulated flexible reamer is passed over the pin. The canal is enlarged by reaming through the upper portion of the femur, then along the canal, across the fracture site, and into the lower portion of the femur, whereupon the rod is driven into the canal.

Reaming of the canal is normally accomplished with flexible reamers and a rotatory drill during the surgical procedure. The procedure may be used for proximal, mid-shaft or distal fractures and in many cases, for oblique and segmented or comminuted fractures. The surgeon utilizes fluoroscopic imaging during the reaming procedure and placement of the rod to ensure proper reduction of the fracture and the proper depth and placement of the rod. It is important to avoid eccentric reaming of the canal which can result in comminution at or near the fracture site. Since the reamers are long and flexible and usually must curve away from the torso of the patient when in use, it will be appreciated by those skilled in the art that avoiding eccentric reaming is a precise and demanding task. It is to the facilitation of this task that the present invention is directed.

SUMMARY OF THE INVENTION

Briefly described, the present invention relates to a femoral wire guide which the surgeon utilizes to hold and stabilize the distal, cutting end of the guide wire at the point of entry into the bone. The instrument allows a firm grip to be maintained on the distal end of the wire as the tip of the wire begins to form a bore in the boney surface, even during rotation of the wire. While dependent to a certain degree on the patient and the type of fracture, once entry into the intramedullary canal is established utilizing the present instrument, rotation of the wire and the reaming function is begun with a cannulated reamer of relatively small diameter, for example, 9 mm. The guide wire inserted with the present instrument is used to guide the reamer into the bone and the medullary canal. The canal is gradually enlarged by using reamers of progressively larger diameter in 0.5 mm or 1 mm increments, enlarging the canal to approximately 12 mm to 16 mm diameter, but which may be larger or smaller diameters depending on the size of the bone.

The present wire guide is designed to be held by the surgeon in one hand while the other hand manipulates the drill which is connected to the initial cutting tip guide wire. This initial step in the canal reaming procedure is most important since the initial guide wire insertion into the surface of the bone forms the entry to the canal. The guide wire serves as a guide for the initial end cutting reamer. After reaming with the initial end cutting cannulated flexible reamer, the end cutting guide wire is exchanged for a bead tip guide wire. Reaming is then continued with progressively larger-sized reamers.

The instrument includes an elongated handle means with post means extending radially from a head portion at the distal end of the handle. The post means generally comprise a pair of spaced post members having wire guide means formed therein. The post members are length-extendable such that the distally positioned post can directly engage the piriformis sinus through which the initial canal is formed, for steadying the wire guide instrument and consequently the lengthy guide wire. The spacing and design of the post members is such that the pressure applied by the posts to the distal end of the guide wire effectively maintains the distal end of the guide wire coaxial with the intramedullary canal while the proximal portion of the guide wire curves away from the patient.

It is, therefore, one of the principal objects of the present invention to facilitate the boring of a hole in the proper location for the formation of a canal of a desired diameter through a fractured bone for receiving an intramedullary nail, by providing a femoral wire guide instrument, elements of which hold the guide wire and abut a portion of the bone being drilled for steadying the guide wire.

Another object of the present invention is to provide a femoral wire guide instrument which has adjustable post means for holding an end cutting guide wire for accommodation of various bone sizes and in which the post means are reversible for use on either the right or left leg.

A further object of the present invention is to provide a femoral wire guide that is easily set up and adjusted and which facilitates the demanding task of the orthopedic surgeon of aligning and maintaining the distal end of a guide wire in coaxial relationship with the canal of the bone.

Various additional objects and advantages will become apparent from the following detailed description, with reference to the accompanying drawings.

BRIEF DESCRIPTION OF THE DRAWINGS

FIG. 1 is a perspective view of the present femoral wire guide instrument, illustrating in solid and broken lines the adjustable positioning of the post means;

FIG. 2 is a partial perspective view, shown partially in cross-section, illustrating the instrument in operation;

FIG. 3 is a partial, perspective view of the head portion and post means, similar to FIG. 1 but taken from a slightly different angle;

DETAILED DESCRIPTION OF THE PREFERRED EMBODIMENT

Figure 4:
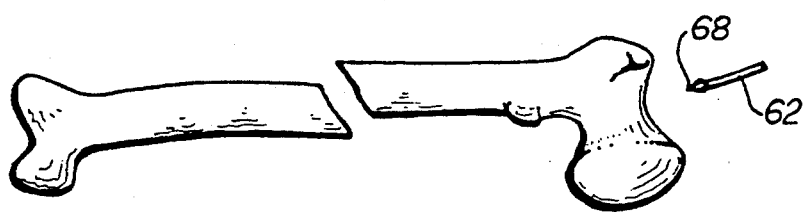
FIG. 4 is a schematic bottom elevational view, illustrating one of the initial steps in repairing a fractured femur.
Figure 5:
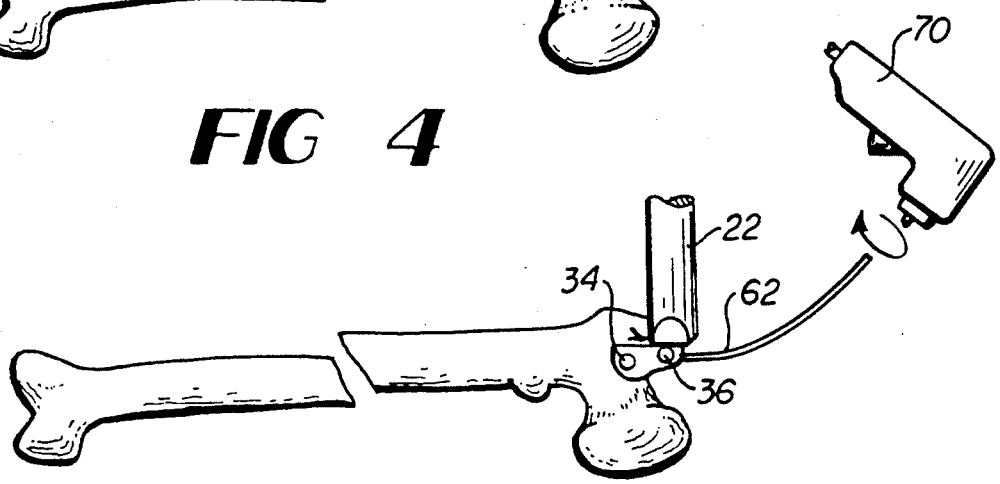
FIG. 5 is a schematic bottom elevational view, illustrating the use of the present instrument during surgery.

Referring now more specifically to the drawings and to FIG. 1 in particular, numeral 20 designates generally the present femoral wire guide instrument. The following detailed description describes the instrument and its use in closed intramedullary rod fixation of the femur in the supine position. Specifically, the present instrument is used to facilitate starting of the initial opening and for the insertion of a guide pin through the piriformis recess in what may be generally termed the trochanteric region.

The instrument 20 is composed of stainless steel or other suitable strong material that is capable of being sterilized. The instrument includes an elongated handle means 22 with a head portion 24 mounted on the proximal end thereof, the longitudinal axis 25 of which is generally at a right angle to the longitudinal axis 27 of the handle. The head is formed with a narrow portion 26 adjacent the handle with a relatively wide portion 28 offset from the handle. Each of the narrow and wide portions of the head include a threaded aperture, 30 and 32 respectively, the apertures and threads extending completely through the head and perpendicular to the handle.

A distal post member 34 is threadedly mounted in aperture 32 and a proximal post member 36 is threadedly mounted in aperture 30. As indicated by the phantom lines in FIG. 1, these post members can be threaded into the apertures from either side. With the post members threaded in from the left side, as viewed in FIGS. 1 and 3, the instrument is configured for use on the right femur of a supine patient. When the instrument is configured with post members threaded in from the opposite side, as shown in broken lines in FIG. 1, the instrument is set up for an operation on the left femur of a supine patient.

The post members are provided with concave groove means 38 and 40 near the outer ends thereof for receiving and directing the guide wire. The distal post member, which is the post member that is closest to the piriformis sinus that is being entered or drilled into, has a straight groove 38 formed in one side thereof. The proximal post member has a circular groove 40 formed completely therearound. As shown in FIG. 2, the straight groove 38 provides a guideway straight into the piriformis sinus 60 for the wire 62, while the circular groove 40 provides a guideway for entering the straight groove 38 and a fulcrum for bowing the wire 62, for keeping the wire taut and for maintaining its position when necessary. The grooves 38 and 40 taken together, form a channel for holding and guiding said wire, and also for effectively dissipating any bending stress on the wire anterior to the straight groove, i.e. between the straight groove and the site of entry into the bone. FIG. 3 illustrates the post members 34 and 36 inserted from the opposite side from that shown in FIG. 2. The view is taken from a different angle also to illustrate the positioning of the wire 62 as it is engaged with the post members so that the function of the post members may be clearly shown and understood. The wire must be flexible because the hole to be formed in the sinus normally is accomplished by drilling with the rotary drill tool 70 that imparts rotary motion to the wire being remotely positioned from the entry site, as shown in FIG. 4. There is very little space for the surgeon to work in and the location of the bone canal and the entry site usually are not in axial alignment with the site of the incision, thus precluding the use of a drill with a straight bit.

The grooves 38 and 40 of the distal and proximal post members 34 and 36 are positioned at a height along the lengths of the post members that will, in the majority of cases, place the distal end of the guide wire in the optimal position when the handle 22 is against the inferior border 64 of the greater trochanter 65, distal in this case being relative to the surgeon. The elongated spade-tip guide wire 62 is locked into the grooves of the post members and held in position by gently bowing the outer or proximal end of the wire 62, (relative to the surgeon) away from the torso of the patient. With an incision having been made, the assembly is placed in the wound so that the distal post 34 is against the medial trochanter 66 and the proximal post is just proximal to the tip of the greater trochanter 65. At this point, the spade tip 68 of the guide wire, shown in FIG. 3, is protruding just past the straight groove 38 to avoid contacting the bone prior to final alignment. The alignment of the wire can be adjusted by rotating and threading the post members in or out of their respective threaded apertures 30 and 32, depending on the size and shape of the bone.

The distal post 34 is pulled into the medial trochanter while upward pressure is applied to hold the wide portion 28 of the head portion 24 against the inferior border of the greater trochanter. This wide portion of the head 24 provides a substantial base for maintaining the head of the instrument against the medial trochanter and prevents its being dislodged from the wound. If the instrument can be pulled out of the wound, it indicates improper positioning. Thus a positive indication is provided for proper positioning.

Referring to FIGS. 2 through 6, a rotary drill tool 70 is attached to the wire 62 and the rotary movement applied by the drill 70 to the wire 62 and the spade-shaped end 68 of the wire causes a bore to be formed in the bone, through the piriformis sinus 60, and into the intermedullary canal 80. The bending stress on the wire as a result of the drilling operation, which would normally be translated to the spade tip 68 and result in eccentric drilling, is thus virtually eliminated by directing the wire between the post members. The post members effectively re-straighten the flexible wire, which has to be bowed away from the patient in order to use the drill, as illustrated particularly in FIGS. 2, 4 and 5. The groove means 38 and 40 of the post members 34 and 36 thus define a straight path into the trochanteric region while allowing the surgeon to operate the drill at a site remote from the piriformis sinus, while maintaining firm and fine control of the wire essentially at the point of entry into the sinus. In addition, it is considered within the scope of the present invention that other means for maintaining control and positioning of the wire may be formed in, or provided as an adjunct to, the post means. Examples of such alternate embodiments may include post means having bores therethrough or having sleeves connected therewith.

If more posterior placement for the guide pin is needed, this is accomplished by holding the handle a desired amount below the level of the inferior border of the trochanter. If the pin needs to be more anterior, the post members are threaded outwardly to effect the adjustment. Changing the instrument from a left side wire guide to a right side wire guide or vice versa, requires a simple reversal of the post members, as illustrated by the broken lines in FIG. 1.

Figure 6:
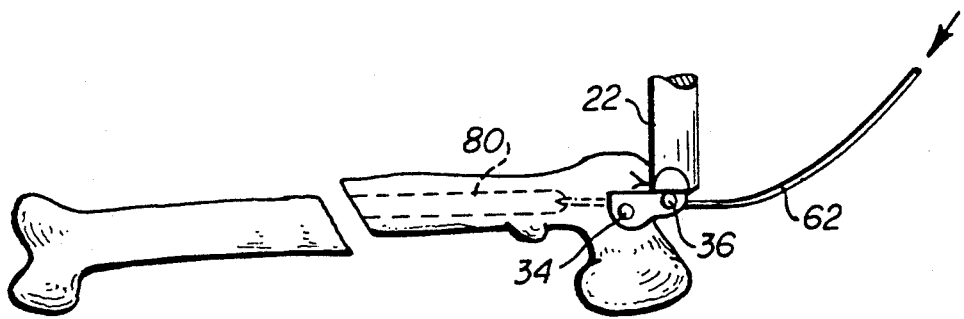
FIG. 6 is a schematic, bottom elevational view illustrating the further use of the present instrument during surgery and the results thereof.
Figure 7:
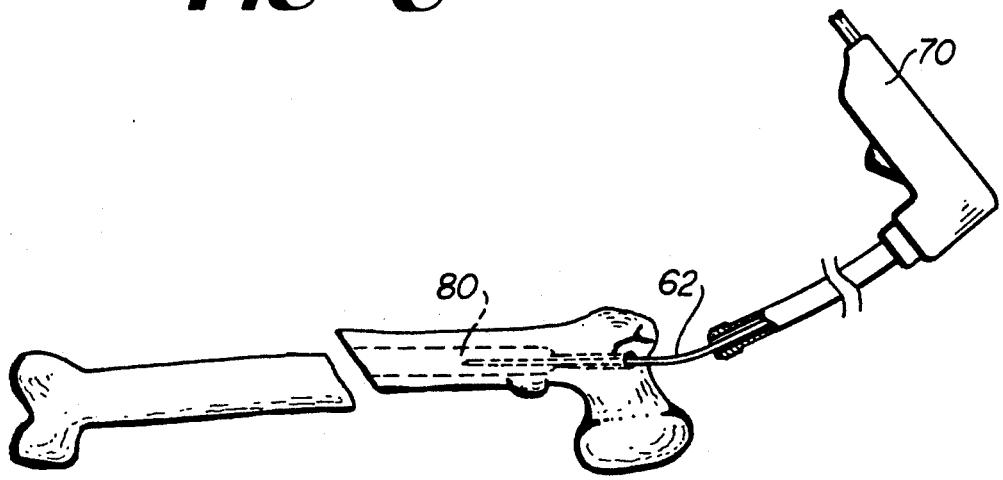
FIGS. 7-12 are schematic views which illustrate in sequence the remaining steps of the operation on the femur, after the present instrument has performed its function.
Figure 8:
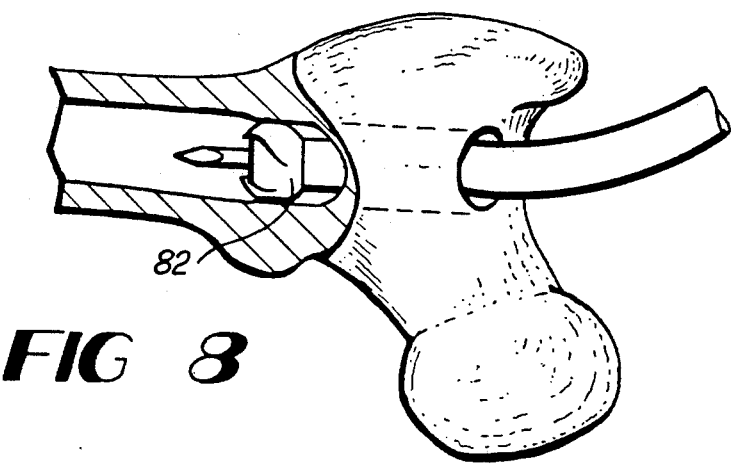
Figure 9:
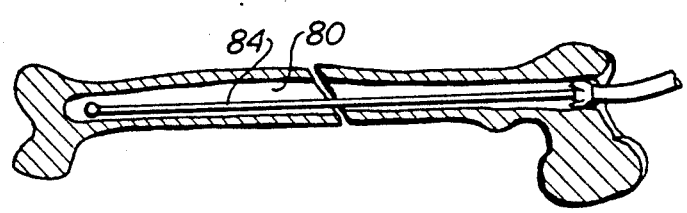

When the wire has reached the intramedullary canal 80, as illustrated in FIG. 6, the wire guide instrument 20 is removed and the position of the pin is checked on lateral and antero-posterial fluoroscopic images to ensure proper alignment and centralization with regard to the canal 80. If the pin is in proper position on antero-posterial and lateral image, it can either be drilled or hammered part of the way down the canal proximal to the fracture. An end cutting reamer 82 is placed over the guide wire and used to further open the bore (FIGS. 6-8). A beaded, guide wire 84 is then exchanged for the end cutting wire and used to cross the fracture site and to serve as a guide for the final reaming of the intramedullary canal, as illustrated in FIG. 9.

Figure 10:
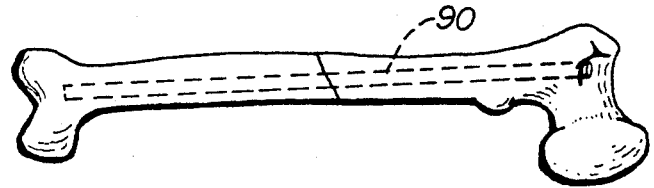
Figure 11:
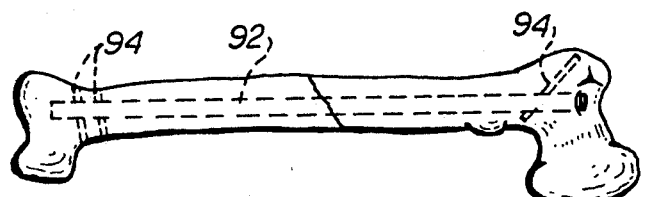
Figure 12:
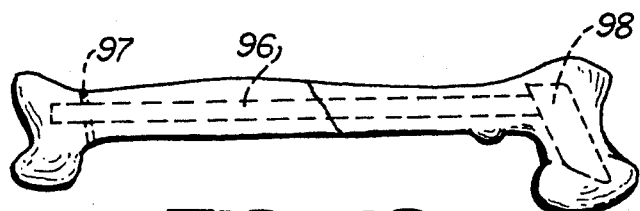

FIGS. 10 through 12 illustrate diagrammatically different ways to secure the bone, having achieved reduction of the fracture. These methods include a single straight nail 90 (FIG. 10), a nail 92 with crossing pins 94 (FIG. 11) or a nail 96 with a pin 97 and plate 98 (FIG. 12). The nails, pins, etc. are often removed after healing of the fracture is complete.

Thus, it is believed apparent from the foregoing detailed description that the present femoral wire guide instrument provides a stable, secure, and novel means for introducing a guide wire from the piriformis sinus in the region of the greater trochanter into the intramedullary canal, this being the most critical portion of the operation procedure.

While an embodiment of a femoral wire guide instrument and modifications thereof have been shown and described in detail herein, various additional changes and modifications may be made without departing from the scope of the present invention.

I claim:

1. An instrument for holding and guiding an elongated wire means while said wire means is being inserted through the region of the piriformis sinus and into the intramedullary canal of a femur, said instrument comprising an elongated handle means adapted to be held by the surgeon during the insertion of said wire means, said handle means having a distal end with a head portion mounted thereon, and wire guide means disposed in said head portion for receiving and steadying said wire means during the insertion operation, said wire guide means including a distal post member for engaging the medial trochanter and steadying said instrument, said distal post member having an outer surface with a substantially straight groove means formed in said outer surface for receiving said wire means, and a proximal post member, spaced from said distal post member and having an outer surface with a groove means formed in said outer surface for receiving said wire means, wherein said groove means provide a substantially straight guideway for entering the piriformis sinus.

2. An instrument as defined in claim 1 in which said wire guide means comprises a pair of spaced post members each having means for maintaining the inserted end of said wire means in substantially axial alignment with the intramedullary canal while the other end of said wire means is bowed out of axial alignment therewith.

3. An instrument as defined in claim 1 in which said groove means are substantially concave in shape for receiving said wire means therein.

4. An instrument as defined in claim 1 in which said groove means in said proximal post member extends around the entire periphery thereof for serving as a fulcrum for bowing said wire means.

5. An instrument as defined in claim 1 in which said head portion includes at least one threaded aperture therein having an axis disposed perpendicular to the longitudinal axis of said handle means and said wire guide means includes a correspondingly threaded portion for threadedly engaging said aperture and projecting radially from said head portion.

6. An instrument as defined in claim 6 in which said wire guide means may be threaded into said aperture from either side for use from either side.

7. An instrument as defined in claim 1 in which said head portion includes a plurality of threaded apertures therein, each having axes disposed perpendicular to the longitudinal axis of said handle means, and said wire guide means includes a plurality of post members corresponding to the number of said apertures, each having threaded portions for threadedly engaging said apertures.

8. An instrument as defined in claim 7 in which said post members may be threaded into said apertures from either side for use from either side.

9. An instrument for holding and guiding an elongated wire means for use in drilling a canal through the trochanteric region of the femur, said instrument comprising a handle means having a longitudinal axis and adapted to be held by the surgeon during the drilling operation, a head portion mounted on said handle and a pair of spaced post members projecting from said head portion, each of said post members having groove means, the groove means of each post member being axially aligned with the groove means of the other post member along the length of the wire means and displaced from one another along the length of the wire means, said groove means having oppositely facing open sides and defining a path for said wire means and being sized and shaped for receiving and guiding the distal end of the wire means along a rectilinear path during the drilling operation while the proximal end of the wire means is bowed out of alignment with the rectilinear path.

10. An instrument as defined in claim 9 in which said groove means together form a channel for holding and guiding said wire means.

11. An instrument as defined in claim 9 in which said post members include a distal member for engaging the medial trochanter and steadying said instrument, said distal post member having a substantially straight groove means formed therein for receiving said wire means, and a proximal post member spaced from said distal post member and having a groove means formed therein for receiving said wire means, wherein said groove means provide a substantially straight guideway for entering the piriformis sinus.

12. An instrument as defined in claim 11 in which said groove means are substantially concave in shape for receiving said wire means therein.

13. An instrument as defined in claim 9 in which said head portion includes at least one threaded aperture therein having an axis disposed perpendicular to the longitudinal axis of said handle means and said wire guide means includes a correspondingly threaded portion for threadedly engaging said aperture and projecting radially therefrom.

14. An instrument as defined in claim 9 in which said head portion includes a plurality of threaded apertures therein, each having axes disposed perpendicular to the longitudinal axis of said handle means, and said wire guide means includes a plurality of post members corresponding to the number of said apertures, each having threaded portions for threadedly engaging said apertures.

15. An instrument for holding and guiding a wire means for use in drilling a canal through the trochanteric region of the femur in an operation to repair a fracture of the femur by fixing a rod in the intramedullary canal, said instrument comprising an elongated handle means adapted to be held by the surgeon during the drilling operation and having a distal end, a head portion disposed on said distal end and mounted generally perpendicular to said handle means, and a pair of wire guide means disposed in said head portion and projecting radially therefrom, said guide means including a distal guide means adapted to engage the piriformis sinus in the trochanteric region for steadying the instrument, said distal guide means having an outer surface portion and a proximal guide means spaced from said distal guide means and also having an outer surface portion, said guide means each including grooves in each of said outer surface portions and having an open side and opposing walls sized and shaped for receiving and guiding said wire means, said grooves also being axially aligned and displaced from one another for defining a straight path for the wire means as the wire means is drilled into the trochanteric region.

16. An instrument as defined in claim 15 in which said wire guide means comprise post members each having a substantially concave groove formed therein for receiving the wire means.

17. An instrument as defined in claim 15 in which said wire guide means comprise axially adjustable post members having groove means formed therein for receiving the wire means.

18. An instrument as defined in claim 15 in which said means for defining a straight path include groove means formed in said wire guide means, said groove means being disposed such that the portion of the wire extending from said proximal guide means to said distal guide means is disposed approximately at a right angle to the longitudinal axis of said handle means.

19. An instrument as defined in claim 15 in which said wire guide means may be threaded into said aperture from either side for use from either side.

* * * * *